June 8, 1937.
S. C BASTON
Plant Pat. 250
LILY OF THE VALLEY PLANT
Filed March 3, 1936
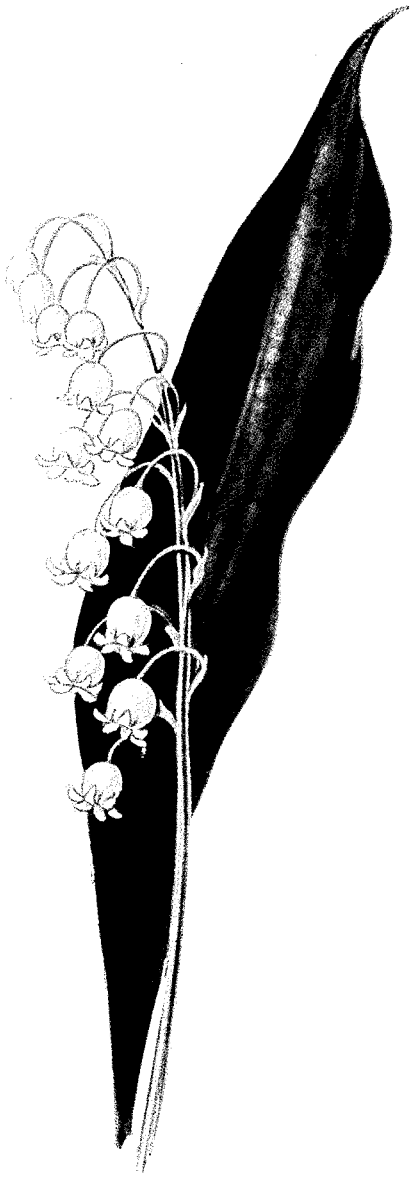
INVENTOR
Sidney C. Baston
Parker, Prochnow & Farmer
ATTORNEYS Patented June 8, 1937

Plant Pat. 250

UNITED STATES PATENT OFFICE

250

LILY OF THE VALLEY PLANT

Sidney C. Baston, Eggertsville, N. Y.

Application March 3, 1936, Serial No. 66,851

1 Claim. (Cl. 47—60)

My new lily of the valley plant corresponds with the well known, common type of lily of the valley (*Convallaria majalis*) in all respects except color.

As shown in the accompanying water color drawing, my new variety is characterized by having a raceme in which the individual flowers or bells have the edges of their petals a light Mallow Purple, (Ridgway Plate XII, 67–d) lighter in center of petals and toward the tips. Bases of cups darkest and those nearest the terminal of the raceme the darkest. Insides white.

Flowers small, 9 mm. diameter, 6 mm. high. 11 to 14 on a stem, averaging 13.

Stems Apple Green to Light Bice Green. 7 in. to 9 in. long. (Ridgway XVII 29′–0 x 29′–i.)

The foliage consists of the usual pair of oblong-lanceolate leaves. They are large 2¼″ x 8¼″ and 2¼″ x 7¼″. Leaves are Bice Green (Ridgway XVII 29′ k.).

The pronounced fragrance is also comparable with that of the common type.

This improved lily of the valley plant, grown under outdoor conditions, has been found to have the same season and period of blooming as that of the common cream-white type, in a given locality.

My new and improved lily of the valley originally appeared as a single plant in a patch of the common variety. This plant was removed, planted by itself, and other plants having the same characteristics were subsequently secured therefrom by root division. The plant is therefore capable of asexual reproduction, and as a result of tests over several years, has been found to hold its color characteristics constant, with no reversion to the cream-white color of the ordinary variety. The stock has been consistently increased by root division until at the present time an ample supply is at hand to meet a limited commercial demand.

I claim as my invention:

A new and improved variety of lily of the valley plant (*Convallaria majalis*; var.), as shown, characterized by having racemes in which the individual flowers have the edges of their petals of light Mallow Purple (Ridgway Plate XII, 67–d) lighter in center of petals and toward the tips, bases of cups darkest and those nearest the terminal of the raceme the darkest, insides white, stems Apple Green to Light Bice Green (Ridgway XVII 29′–0 x 29′–i.), and leaves Bice Green (Ridgway XVII 29′k.).

SIDNEY C. BASTON.